United States Patent [19]

Boodman et al.

[11] 4,034,048
[45] July 5, 1977

[54] TAR ACID PRODUCTS FROM SOLVENT NAPHTHA

[75] Inventors: Norman S. Boodman, Penn Hills Township, Allegheny County; Richard C. Weil, Monroeville Borough, both of Pa.

[73] Assignee: United States Steel Corporation, Pittsburgh, Pa.

[22] Filed: Nov. 15, 1971

[21] Appl. No.: 198,967

[52] U.S. Cl. .................. 260/621 H; 260/621 D; 260/627 R
[51] Int. Cl.² .................. C07C 37/32; C07C 39/02
[58] Field of Search ....... 260/624 R, 627 R, 627 H, 260/621 D, 621 H, 627 B, 624 C, 621 R

[56] References Cited

UNITED STATES PATENTS

| 1,208,833 | 12/1916 | Ramage | 260/621 D |
| 1,947,648 | 2/1934 | Hofmann et al. | 260/621 D |
| 2,998,457 | 8/1961 | Paulsen | 260/621 |
| 3,321,393 | 5/1967 | Schuman et al. | 260/627 H |

FOREIGN PATENTS OR APPLICATIONS

| 679,916 | 2/1964 | Canada | 260/621 H |
| 999,472 | 7/1965 | United Kingdom | 260/624 R |

OTHER PUBLICATIONS

Winter et al., "Chem. Abs.", vol. 31, p. 2785 (1937).

*Primary Examiner*—James O. Thomas, Jr.
*Assistant Examiner*—W. B. Lone
*Attorney, Agent, or Firm*—William L. Krayer

[57] ABSTRACT

Solvent naphtha is hydrogenated over an alumina-supported cobalt molybdate or nickel molybdate catalyst to produce tar-acid products.

6 Claims, No Drawings

TAR ACID PRODUCTS FROM SOLVENT NAPHTHA

BACKGROUND OF THE INVENTION

There is present in coal, especially the lower rank coals, a relatively high oxygen content, present in all probability as ether linkages bonding the cyclic structures. Carbonization of the coal, at low or high temperatures, ruptures these linkages and reforms the fragments to produce the different tar-acid molecules found in the resulting low- and high-temperature tars. Also produced during this reforming process are oxygen-containing heterocyclic ethers, such as benzofuran, more commonly known as coumarone. High temperature carbonization of bituminous coal, as practiced for production of metallurgical coke, produces coumarone which is recovered in the light-oil fractions from the coke-oven gas and the condensed tar. The work-up of the light-oil fractions to recover monocyclic aromatics such as benzene, toluene and xylene, results in isolation of an intermediate distillate product having a boiling point in the range of about 160° to 200° C, which is commonly referred to as the solvent naphtha fraction. A typical analysis of this fraction is given in Table I.

Table I

| Analysis of Solvent Naphtha Fraction | |
|---|---|
| Component | Percent[1] |
| Unidentified (prob. aliphatics) | 3.2 |
| m, p-Ethyltoluene | 1.2 |
| 1,3,5-Trimethylbenzene & o-ethyltoluene | 5.1 |
| 1,2,4-Trimethylbenzene | 11.0 |
| α-Methylstyrene & 1,3-dimethyl-5-ethylbenzene | 0.8 |
| 1,2,3-Trimethylbenzene & m,p-vinyltoluene | 7.1 |
| Indane | 1.5 |
| Unidentified | 0.5 |
| Indene | 58.7 |
| Coumarone[2] | 8.6 |
| Benzonitrile | 2.2 |
| Unidentified | 0.2 |
| Tar Acids (nonaqueous titration), milliequivalents per 100 grams | 1.0 |

[1]By gas-chromatographic analysis.
[2]Contains small proportion of methylcoumarones.

This fraction, rich in indene, a polymerizable compound, was in the past marketed for its resin-formers content. Coumarone-indene copolymer produced from the solvent naphtha fraction is a low-cost resin that once found extensive use in the manufacture of coatings and floor-coverings. However, the development of improved synthetic materials such as polyvinyl chloride has resulted in displacement of the coumarone-indene resins from these applications. Because of the large concentration of polyalkylbenzenes, as well as indene, in the solvent naphtha fraction, it was believed that an effective hydrocarbon solvent could be prepared by hydrogenation of the fraction. However, prior to the ring hydrogenation, it is first necessary to destroy the heterocyclic contaminants that otherwise would poison and inactivate conventional hydrogenation catalysts. This destruction is generally achieved by a hydrorefining reaction in which the feed is subjected to a hydrogenating atmosphere at elevated temperature and pressure and with a special refining catalyst that is capable of promoting the desired elimination reactions.

The major heterocyclic contaminant in solvent naphtha is coumarone (benzofuran). Under conventional hydrorefining conditions the following reaction would be expected to occur:

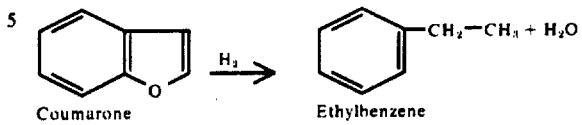

Thus, Shuikin, et al, Chem. Abstr., 33: 1316[1,2] (1939), and Shuikin et al, Chem. Abstr., 35: 2508[5] (1941), examining the hydrogenation of pure furan, alkylfuran and benzofuran, found that the furans were converted to their corresponding tetrahydro derivatives when passed with hydrogen over a nickel aluminum catalyst (27% Ni - 73% Al) at 120° to 140° C.

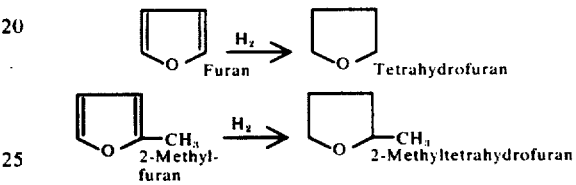

Using benzofuran and the same catalyst, the product formed was purported to consist of a mixture of 2-ethylcyclohexanol and β-cyclohexylethyl alcohol.

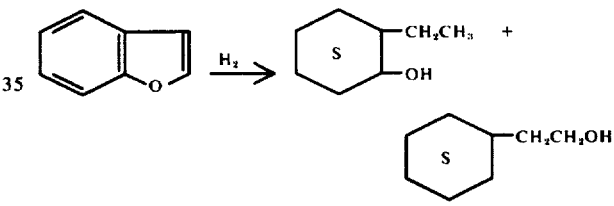

It is seen that hydrogenolysis under these conditions yields an alcohol resulting from saturation hydrogenation of the aromatic ring or a β-substituted alcohol resulting from cleavage between the O-atom and the ring.

SUMMARY OF THE INVENTION

We have now discovered, quite unexpectedly, that the coumarone in the solvent naphtha fraction, together with the small concentration of methylcoumarones present, is almost quantitatively converted to mainly orthoalkyl-substituted tar-acid products when alumina-supported nickel or cobalt molybdate is employed as the refining catalyst. This result is even more surprising in light of the fact that other conventional hydrorefining catalysts such as molybdenum sulfide behaved as expected by destroying the coumarone but without formation of tar acids.

DETAILED DESCRIPTION

In our process, hydrogenolysis occurs selectively between the O-atom and the α-carbon on the heterocyclic ring. Ring saturation does not occur. The major products of our reaction are ortho-ethylphenol, ortho-cresol and phenol, the last two of which are derived by successive demethylation reactions.

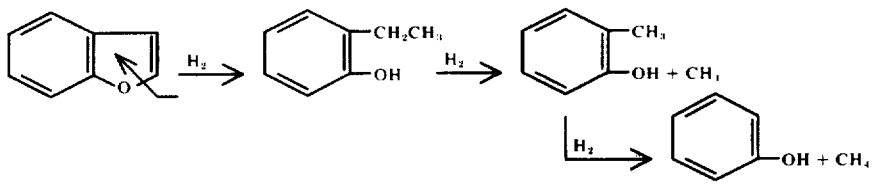

The conversion of coumarone to tar acids according to our process is accomplished by adding the solvent naphtha fraction to a pressure vessel containing alumina-supported nickel molybdate or cobalt molybdate catalyst. The reaction occurs at a temperature in the range of about 300° to 500° C and a pressure of at least 1000 psig of hydrogen. We prefer to conduct the reaction at a temperature in the range of about 350° to 475° C and a hydrogen pressure of 1000 to 3000 psig. Best results are obtained when the temperature is in the range of about 400° to 450° C and the hydrogen pressure is in the range of about 1500 to 2000 psig. Below about 300° C the hydrogenolysis reaction is too slow to be of practical importance, while above 500° C, feed coking and gasification become the predominant reactions. The reaction is kinetically and thermodynamically favored by increased pressure. At pressures below 1000 psig, care must be taken to avoid temperatures at the high end of the operational range lest coking or gasification become significant side reactions. There is no limitation on the high pressure side other than that imposed by equipment and other cost considerations.

The catalyst concentration may vary widely. Generally, a catalyst concentration in the range of about 1 to 20 percent by weight of the light oil fraction gives good results. We have found that catalyst concentrations in the range of 6 to 12 percent give best results.

The reaction proceeds more smoothly when the pressure vessel is agitated either by rocking the entire vessel or by internal agitation.

The reaction time in a batch-operating system is not of critical importance and is governed principally by the heat-up and cool-down times. Two hours at operating temperature is more than sufficient to effect the desired transformation.

The hydrorefining reaction could also be performed in a continuous refining unit with a fixed bed catalytic reactor. A contact time of about 5–10 minutes should be sufficient, with a hydrogen-to-oil ratio of between about 3 to 1 and 10 to 1, preferably between 4 to 1 and 8 to 1.

Under the reaction conditions specified, conversion of the coumarones is quantitative, and no saturation hydrogenation of the tar acids occurs. The tar acids formed by this reaction technique may be recovered from the refined naphtha fraction by any of the conventional means practiced. For example, they may be extracted from oil with dilute aqueous caustic and the caustic extract rectified and sprung with carbon dioxide or dilute mineral acid.

Phenol and ortho-cresol are well-defined products with established uses. Ortho-ethylphenol is an analog of ortho-cresol and may be substituted for it in many applications. For example, it can be nitrated to prepare effective insecticides or it may be used as is as a modifier in phenol-formaldehyde resins. It may also be mono-t-butylated to form a rubber antioxidant or stabilizer for nonedible fats, greases and insulating oils. It can be chlorinated to prepare useful bactericides and fungicides. The heavier tar acids with or without the ortho-ethylphenol may be used as a special cresylic solvent for ore flotation, metal cleaning or as a solvent extraction agent for refining lubricating oils.

Our invention is further illustrated by the following non-limiting examples.

EXAMPLE 1

To a 1-gallon rocking autoclave were charged 930 grams of solvent naphtha having the composition listed in Table I and 139.5 grams (15 weight percent) of an unsupported molybdenum sulfide catalyst. The autoclave is closed and pressurized to about 1200 psig with hydrogen. The mixture was allowed to react for 2 hours at a temperature of 410° C and pressure of 2000 psig hydrogen. The product mixture was cooled, removed from the vented autoclave and filtered. The filtered raffinate had no detectable tar acids (by nonaqueous titration) indicating completeness of conversion of the coumarone to ethylbenzene.

EXAMPLE 2

The 1-gallon autoclave was charged with 1011 grams of solvent naphtha having the composition listed in Table I and 101 grams (10 weight percent) of alumina-supported nickel molybdate catalyst (American Cyanamid, Aero HDS-3). The mixture was reacted for 4.5 hours at a temperature of 410° C and pressure of 2000 psig hydrogen, and the product mixture was worked up as in Example 1. Analyses of the raffinate and tar-acid extract are shown in Tables II and III. Conversion of the coumarone was quantitative, and the tar-acids content increased from 1.0 milliequivalent per 100 grams (before hydrorefining) to 74.5 (after). Analysis of the tar-acid concentrate showed ortho-ethylphenol to be the major component (58%), followed by ortho-cresol (22%) and phenol (7%).

EXAMPLE 3

The autoclave was charged with 1000 grams of solvent naphtha having the composition listed in Table I and 100 grams (10 weight percent) of alumina-supported cobalt molybdate catalyst (American Cyanamid, Aero HDS-2). Reaction conditions were 410° C, 2000 psig hydrogen and 4.5 hours reaction time. The formed tar acids (64.9 milliequivalents per 100 grams) were extracted from the raffinate and analyzed, Table IV. The same types and approximate relative amounts of the individual tar acids were obtained.

Table II

| Analysis of Hydrorefined Solvent Naphtha Fraction[1] | |
|---|---|
| Component | Percent[2] |
| Unidentified | 0.7 |
| Toluene & unidentified | 0.5 |
| Unidentified | 0.9 |
| Ethylbenzene | 1.1 |
| m,p-Xylene | 0.7 |
| Cumene | 0.4 |
| o-Xylene | 0.3 |

Table II-continued

Analysis of Hydrorefined Solvent Naphtha Fraction[1]

| Component | Percent[2] |
|---|---|
| n-Propylbenzene | 0.8 |
| m,p-Ethyltoluene | 3.9 |
| 1,3,5-Trimethylbenzene & o-ethyltoluene | 4.8 |
| 1,2,4-Trimethylbenzene & unidentified | 11.6 |
| 1,2,3-Trimethylbenzene & 1,3-dimethyl-5-ethylbenzene | 2.7 |
| Indane & 2-methylindane | 58.4 |
| 1-Methylindane | 3.7 |
| Prob. durene & isodurene | 0.1 |
| Prob. 5-methylindane | 0.1 |
| Prob. 4-methylindane | 0.4 |
| Tetralin | 0.2 |
| Unidentified (minimum 10 compounds) | 0.2 |
| Naphthalene | 0.1 |
| Unidentified | 0.1 |
| Prob. 2,6-Xylenol | 0.1 |
| Phenol & o-cresol | 2.6 |
| Prob. 2-methyl-6-ethylphenol | 0.4 |
| o-Ethylphenol & unidentified | 4.6 |
| Unidentified (prob. tar acid) | 0.4 |
| Unidentified (prob. tar acid) | 0.2 |
| Unidentified | 0.1 |

[1]Hydrorefining catalyst was cobalt molybdate-on-alumina.
[2]By gas-chromatographic analysis.

Table III is an analysis of the tar acids of Table II after they have been extracted with caustic.

Table III

Analysis of Tar Acids from Hydrorefined Solvent Naphtha[1]

| Component | Percent[2] |
|---|---|
| Unidentified | <0.1 |
| Phenol | 7.3 |
| o-Cresol | 22.1 |
| m,p-Cresol | 0.9 |
| o-Ethylphenol & 2,4- and 2,5-Xylenol | 58.1 |
| 3,5-Xylenol & m,p-ethylphenol | 1.9 |
| o-Isopropylphenol | 3.3 |
| 3,4-Xylenol & o-propylphenol | 2.3 |
| m,p-Isopropylphenol | 1.7 |
| 3-Ethyl-5-methylphenol | 0.8 |
| 3-Isopropyl-5-methylphenol & unidentified | 1.6 |
| Prob. 4- and 5-indanol | <0.1 |

[1]From nickel molybdate-catalyzed reaction.
[2]By gas-chromatographic analysis.

Table IV

Analysis of Tar Acids from Hydrorefined Solvent Naphtha[1]

| Component | Percent[2] |
|---|---|
| Unidentified | 0.6 |
| Phenol | 9.6 |
| o-Cresol | 21.9 |
| m,p-Cresol | 1.5 |
| 2,6-Xylenol | 3.2 |
| o-Ethylphenol | 45.4 |
| m,p-Ethylphenol & 3,5-Xylenol & o-isopropylphenol | 1.5 |
| Prob. m,p-Isopropylphenol & 2,4,6-trimethylphenol | 5.6 |
| Prob. 2-ethyl-4-methylphenol & o-propylphenol | 2.9 |
| Prob. methylethylphenols | 4.4 |
| Prob. 4- & 5-indanol | 3.5 |

[1]From cobalt molybdate-catalyzed reaction.
[2]By gas-chromatographic analysis.

We claim:

1. A process for the preparation of tar acids from the solvent naphtha fraction having a boiling point in the range of about 160° – 200° C obtained from the carbonization of bituminous coal, said fraction containing coumarone as the major heterocyclic ingredient, comprising destructively hydrogenating the solvent naphtha fraction over a catalyst selected from the group consisting of alumina-supported cobalt molybdate and alumina-supported nickel molybdate wherein
   a. the temperature is from about 300° C to about 500° C,
   b. the hydrogen pressure is 1000 to 3000 psig, and
   c. the catalyst comprises about 1 – 20 percent by weight of the solvent naphtha fraction.

2. The process of claim 1 wherein the temperature is from about 350° C to about 475° C and the pressure is from about 1000 to about 3000 psig.

3. The process of claim 1 wherein the temperature is from about 400° C to about 450° C and the pressure is from about 1500 to about 2000 psig.

4. The process of claim 1 wherein the hydrogen-to-oil ratio is between about 3 to 1 and 10 to 1.

5. The process of claim 1 wherein the hydrogen-to-oil ratio is between about 4 to 1 and 8 to 1.

6. The process of claim 1 wherein the catalyst comprises 6 – 12 percent by weight of the solvent naphtha fraction.

* * * * *